United States Patent [19]

Goosen et al.

[11] Patent Number: 4,942,129
[45] Date of Patent: Jul. 17, 1990

[54] MULTIPLE MEMBRANE MICROENCAPSULATION

[75] Inventors: Matheus F. A. Goosen, Kingston; Glenn A. King, Peterborough; Andrew J. Daugulis; Peter Faulkner, both of Kingston, all of Canada

[73] Assignee: Queen's University at Kingston, Kingston, Canada

[21] Appl. No.: 218,589

[22] Filed: Jul. 12, 1988

Related U.S. Application Data

[63] Continuation-in-part of Ser. No. 78,628, Jul. 28, 1987.

[51] Int. Cl.⁵ ............................................. C12N 11/04
[52] U.S. Cl. .................................... 435/182; 435/174; 435/240.22
[58] Field of Search ................... 435/174, 181, 240.22

[56] References Cited

U.S. PATENT DOCUMENTS

| | | | |
|---|---|---|---|
| 4,251,387 | 2/1981 | Lim et al. | 435/182 |
| 4,257,884 | 3/1981 | Lim | 435/182 |
| 4,352,883 | 10/1982 | Lim | 435/240.22 |
| 4,391,909 | 7/1983 | Lim | 435/240.22 |
| 4,407,957 | 10/1983 | Lim | 435/182 |
| 4,409,331 | 10/1983 | Lim | 435/182 |
| 4,495,288 | 1/1985 | Jarvis, Jr. et al. | 435/182 |
| 4,582,799 | 4/1986 | Jarvis, Jr. | 435/240.22 |
| 4,778,749 | 10/1988 | Vasington et al. | 435/240.22 |
| 4,803,168 | 2/1989 | Jarvis, Jr. | 435/240.22 |

Primary Examiner—Robert J. Warden
Assistant Examiner—Timothy M. McMahon
Attorney, Agent, or Firm—Richard J. Hicks

[57] ABSTRACT

Living tissues, such as hybridoma cells or insect cells suspended in a water soluble gelling agent, are microencapsulated in a double polymeric membrane microcapsule. The inner membrane is of a high molecular weight cut-off to permit outward diffusion of the gelling agent and also expansion of the microcapsule before formation of the outer membrane which is a relatively lower molecular weight cut-off. The living cells in the dual membrane microcapsule may be grown to an intracapsular density which is significantly higher than that which can be achieved by using single-membrane capsules. The recovery of intracapsular protein product (produced by the encapsulated cells) is also significantly higher and the loss of product through the membrane wall markedly lower for the dual membrane capsule than for the single membrane capsule.

24 Claims, 4 Drawing Sheets

MULTIPLE MEMBRANE MICROENCAPSULATION

CROSS REFERENCE TO RELATED APPLICATIONS

This application is a continuation-in-part of commonly assigned U.S. patent application Ser. No. 078,628 filed 28 July 1987.

FIELD OF THE INVENTION

This invention relates to a method for producing proteins from animal cell cultures. More particularly this invention relates to a microencapsulation process for producing proteins such as antibodies or hormones in vitro.

BACKGROUND OF INVENTION AND PRIOR ART

Conventional suspension cultures for the production of such proteins as antibodies and hormones in vitro are limited in their applicability to large scale use by reason of the low cell densities ($10^6$ cells/ml) which are possible. Relatively large and complex fermentors are required for commercial production with consequent heavy capital expenditures, and even then the concentration of desired product is quite low. Further, most cell lines grow best in serum supplemented medium, but serum proteins greatly complicate the downstream purification of desired protein products from supplemented media.

Alternative processing has therefore been suggested and emphasis has been laid upon microencapsulation to overcome the problems of low cell density and downstream processing. In this process, which has been extensively described in the open scientific literature and in numerous patents, living cells are entrapped within a semipermeable polymer membrane. The living cells are mixed with sodium alginate and extruded into calcium chloride to form calcium alginate gel droplets. The gelled droplets are then reacted with a polyamino acid such as poly-l-lysine (PLL) to form a semipermeable capsule membrane. The interior is then liquified by incubating the capsules in sodium citrate. The encapsulated cells, such as hybridoma cells are then transferred to a suitable medium and incubated for two to three weeks. The concentration and purity of the product is about 100 fold higher than can be achieved by conventional cell suspension cultures. Attention is directed to:

U.S. Pat. Nos. 3,157,631
U.S. Pat. Nos. 3,780,195
U.S. Pat. Nos. 4,251,387
U.S. Pat. Nos. 4,255,411
U.S. Pat. Nos. 4,257,884
U.S. Pat. Nos. 4,322,311
U.S. Pat. Nos. 4,324,683
U.S. Pat. Nos. 4,352,883
U.S. Pat. Nos. 4,386,895
U.S. Pat. Nos. 4,389,419
U.S. Pat. Nos. 4,391,909
U.S. Pat. Nos. 4,407,957
U.S. Pat. Nos. 4,409,331
U.S. Pat. Nos. 4,487,758
U.S. Pat. Nos. 4,495,288
U.S. Pat. Nos. 4,582,799 which are considered to be generally relevant to the process of microencapsulation described hereinabove. It has, however, been established (Posillico, *Biotechnology*, 4, 1986) that cells entrapped within the single membrane capsule of the prior art tend to grow preferentially near the interior surface of the microcapsule. By the end of the culture period the cells cover about one half to three quarters of the interior capsule surface but less than one third of the total capsule volume is occupied by the cells: the other two thirds being occupied by calcium and sodium alginate polymer. It is apparent, therefore, that only part of each microcapsule is available for cell growth as the alginate (Mv $10^5$ to $10^6$) is entrapped within the capsule which has a membrane molecular weight cut-off of about $60 \times 10^3$ to $80 \times 10^3$ in order to entrap the antibody. Further, when the capsules are ruptured to recover the product the entrapped alginate has to be separated out from the suspension of ruptured cells and proteins. There is, therefore, a need for an improved process for significantly increasing the intracapsular cell density and for removing the alginate core prior to incubation of the microcapsules.

SUMMARY OF THE INVENTION

In accordance with the present invention it has now been found that at least one third of the alginate core may be removed by using a three stage procedure which results in the formation of a dual membrane microcapsule. This compares with 11% alginate removal for the single membrane capsule of the prior art.

Thus, by one aspect of the invention there is provided a biocompatible microcapsule, having a diameter of about 400–1500 m, comprising:

A macromolecular core material comprising living tissue surrounded by a first biocompatible highly permeable hydrogel membrane consisting of ionically interacted biocompatible materials, having a molecular weight cut-off of about $200-400 \times 10^3$ and said first membrane being interacted with ionically interacted biocompatible materials, to form a second relatively less permeable hydrogel membrane having a molecular cut-off of about $40-80 \times 10^3$; said first membrane being sufficiently permeable to permit diffusion therethrough of that portion of a water soluble cross-linkable gelling agent used to suspend said living tissue and having a molecular weight of less than $200-400 \times 10^3$, and permitting expansion of said microcapsule towards an equilibrium state; and said interacted membrane being sufficiently permeable to permit nutrients to flow from a medium in which said microcapsule is placed into said microcapsule to sustain said living tissue, and sufficiently impermeable to retain said living tissue and any high molecular weight product thereof within the microcapsule.

By another aspect of the invention there is provided a method of encapsulating living tissue within at least one semi permeable hydrogel membrane which comprises:

(a) mixing said living tissue with an aqueous solution of a water soluble polymeric material which can be reversibly gelled and which has free acid groups:

(b) forming said mixture into droplets and gelling said droplets in a hardening agent:

(c) forming a first biocompatible highly permeable hydrogel membrane about said gelled droplets to produce a first microcapsule by reaction with a polymer containing free amino groups: said first membrane having a molecular weight cut-off of $200-400 \times 10^3$.

(d) suspending said first microcapsule in a medium which reliquifies said water soluble polymeric material:

(e) incubating said first microcapsule in an aqueous medium for sufficient time to allow at least one third of that portion of said water soluble polymeric material having a molecular weight of less than $200-400\times10^3$ to diffuse out of said microcapsule, . and to allow said microcapsule to expand towards an equilibrium state;

(f) reacting said incubated first microcapsule with a polymer containing positively charged groups to thereby form an interacted relatively less permeable membrane having a molecular weight cut-off of $40-80\times10^3$; and (g) incubating said living tissue within said interacted microcapsule in a nutrient medium; said interacted membrane being sufficiently permeable to permit passage of nutrients and sufficiently impermeable to retain said tissue and any high molecular weight products therof within said second microcapsule.

GENERAL DESCRIPTION OF INVENTION

Figure 1:
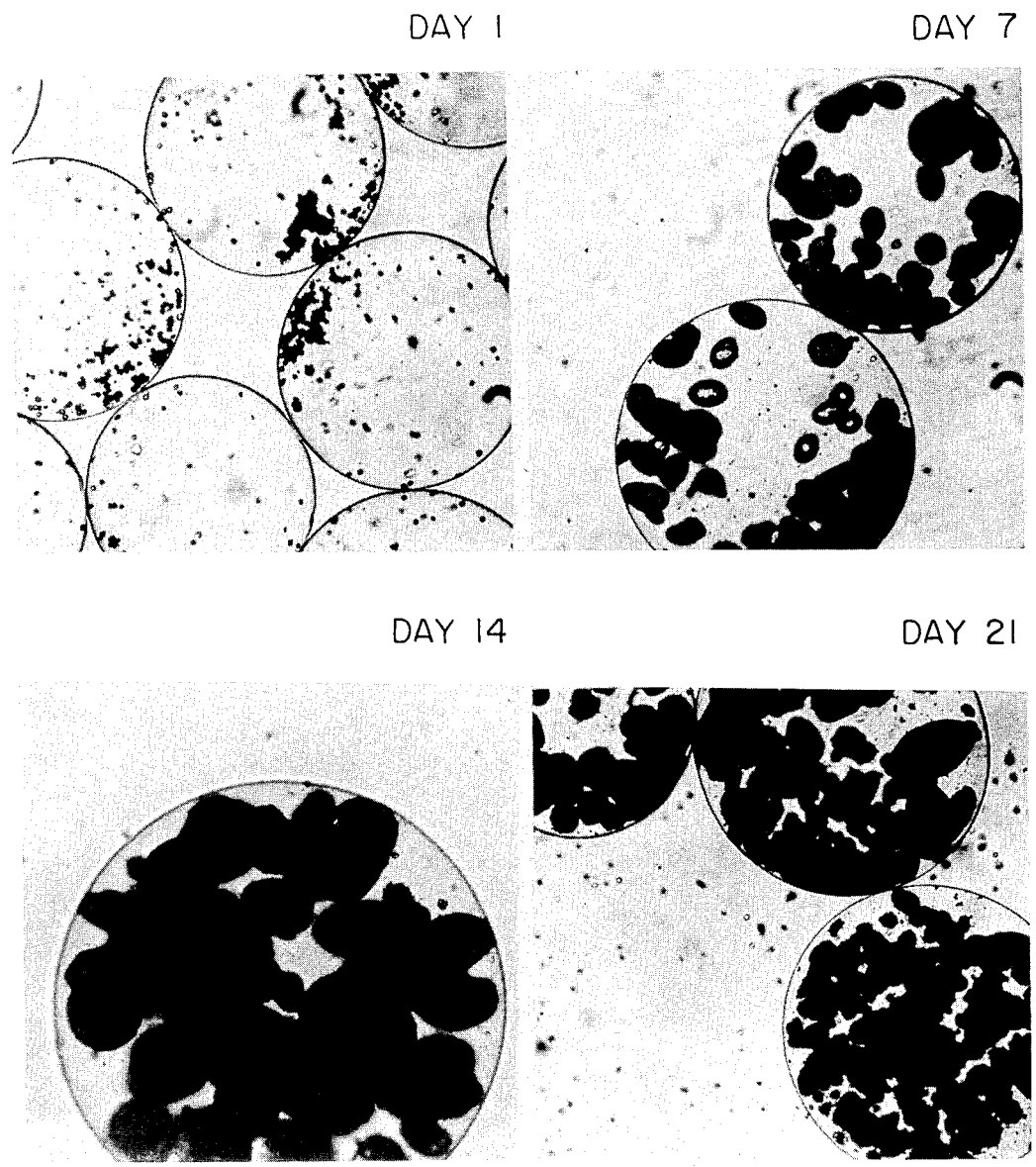
FIG. 1 is a photograph illustrating tissue culture of encapsulated mouse hybridoma cells using a single alginate-PLL membrane with a MW cut-off of 60,000, over a 21 day period.

As noted above the present invention contemplates a dual membrane encapsulation process which comprises four essential steps. Firstly, the living cells to be cultured are mixed with sodium alginate (a seaweed extract and polyanion) and extruded into calcium chloride so as to form gel beads or droplets. Secondly, the gel beads are reacted with a high molecular weight (MW $60-500\times10^3$) concentration (0.03-0.1% w/v) polyamino acid, such as poly-1-lysine, for a period of time (0.05-0.67 hrs) and then the interior of the capsule thus formed is reliquified by treating with sodium citrate. The single membrane thus formed is highly permeable (MW cut-off $200-400\times10^3$). Thirdly the single membrane, highly permeable capsule thus formed is incubated in a saline solution for up to a few hours to allow a greater fraction of the entrapped sodium alginate to diffuse out and to expand the capsule towards an equilibrium state. Fourthly, the alginate-poor highly permeable capsule is then reacted with a low molecular weight polyamino acid (MW $10-30\times10^3$) such as poly-1-lysine (PLL) or chitosan (deacetylated chitin) of $\overline{M}=240\times10^3$ produced by reaction with 0.05 mole sodium nitrate per mole chitosan ($\overline{M}=1210\times10^3$) in a concentration of 0.01-0.03% (w/v) polymer for a period of time (0.05-0.67 hrs) to produce an interacted, less permeable membrane (MW cut-off $40-80\times10^3$). The dual membrane encapsulated cells are then cultured in medium for two to three weeks as in the prior art. At this time it is not entirely clear whether the interacted membrane is a second membrane overlying the first membrane or merely an altered and less . permeable form of the first membrane.

While reference has been made specifically to sodium alginate beads, it will be appreciated by those skilled in the art that any non-toxic water soluble substance that can be gelled to form a shape-retaining mass by a change in conditions in the medium in which it is placed may be employed. Such gelling material also comprises plural groups which are readily ionized to form anionic or cationic groups, so that the surface layers can cross link to form a permanent membrane when exposed to polymer containing functionalities of the opposite charge. Most polysaccharide gums, both natural and synthetic, fall in this class of negatively charged groups such as carboxyl or hydroxyl groups and can be cross linked by polymers containing positively charged reactive groups such as amino groups. Thus, the preferred gum is an alkali metal alginate, specifically sodium alginate, although other water soluble gums may be used. The cross linking biocompatible polymers which may be reacted with the sodium alginate gum, include polylysine and other polyamino acids. Polyethyleneimine and other imine-containing polymers are not biocompatible and should not be used. The degree of permeability of the membrane formed may be controlled by careful selection of a polyamino acid having the desired molecular weight. Poly-1-lysine (PLL) is the preferred polymeric material but others include chitosan and polyacrylate. Molecular weights typically vary from about $10^4$ to about $10^6$.

The process of the invention may be used to encapsulate living tissue or multicellular fractions thereof or individual cells such as islets of Langahans, living cells, red blood cells insect cells, plant cells and hybridoma cells. The capsules protect the cells contained within them, for example, they can protect transplanted insulin-producing islets of Langahans from immune rejections. Encapsulated hybridoma cells such a mouse hybridoma cells can be used to produce multiple gram-quantities of monoclonal antibodies for numerous uses including anti-Rabies activity.

DESCRIPTION OF PREFERRED EMBODIMENTS

In one preferred embodiment, living liver cells or mouse hybridoma cells are encapsulated within a poly-1-lysine-alginate semipermeable hydrogel by suspending cells uniformly in a sodium alginate solution in physiological saline (viscosity 30-100 cps) to obtain a .perfectly spherical shape. Spherical droplets are produced using a conventional droplet generator and collected in a calcium chloride hardening solution. The microcapsules are then incubated in 0.03-0.1% (w/v) poly-l-lysine lysine in saline (MW $60-500\times10^3$) for 3-40 minutes followed by reaction with a dilute alginate solution. The microcapsules are then suspended in an isotonic sodium citrate solution for 4-12 minutes to liquify the interior within a highly permeable membrane having a molecular weight cut-off of about $300\times10^3$. The highly permeable single membrane microcapsules are then incubated in isotonic saline for about 0.5-2 hours to allow sodium alginate to diffuse out through the membrane and to allow the microcapsule to . expand toward its equilibrium state. The microcapsules are then incubated in 0.01-0.1% (w/v) poly-l-lysine (MW $10-30\times10^3$) for 0.05-0.67 hrs to form a second less permeable membrane having a molecular weight cut-off of about $60\times10^3$. The microcapsules thus produced have diameter of between 400 and 1500 pm, preferably 600-800 μm. The thickness of the inner High MW cut-off membrane and outer Low MW cut-off membrane is of the order of 5 μm. The microcapsules can then be incubated in a medium (Dulbeco's Modified Eagles Medium) at 37° C. for a period of one to three weeks in a 5% $CO_2$/95% air atmosphere, to grow the encapsulated cells to an intracapsular density which is significantly higher (200–500%) than that which can be achieved using single membrane capsules. After washing and rupturing the dual membrane capsules (to release the cells and cell products) up to 500% greater recovery of monoclonal antibody product can be obtained.

In a second preferred embodiment, insect cells (*Spodoptera frugiperda*, designated IPLB-SF-21) derived from pupal ovaries of the moth *S. frugiperda*, infected with a temperature-sensitive mutant of the *Autographa californica* Nuclear Polyhedrosis Virus (AcNPV ts-10), which can be maintained at 27° C. in TC100 medium supplemented with 50 μg/ml gentamicin sulphate and 10% v/v heat inactivated fetal calf serum, are encapsulated in the PLL-alginate system described above to form single and multiple membrane microcapsules. Preferably, the composition of the maintenance medium during the encapsulation process is 2×TC100, the composition of which is described in detail hereinafter, and which does not contain either divalent salts (Ca++ or Mg++) which gel sodium alginate, or fetal calf serum. In addition the alginate concentration used in the encapsulation procedure should be less than 0.75% w/v.

EXAMPLE 1

Microencapsulation of Hybridoma Cells in Single Membrane Capsules

In the encapsulation procedure, a sodium alginate solution was mixed with a hybridoma cell pellet. The pellet was prepared by taking 5 mL of cell culture suspension containing cells which had been grown to confluence (i.e. cell density $2\times 10^6$ cells/mL), centrifuging the cell suspension at 1000 rpm for 5 minutes, and decating the medium. The cell pellet remaining at the bottom of the centrifuge tube was then resuspended in 5 mL of a 1.5% (w/v) sodium alginate solution (Keltone LV ® by Kelco Ltd., Chicago Ill.). The alginate/cell suspension was extruded into 50 mL of a 1.5% (w/v) $CaCl_2$ solution Spherical droplets of this suspension were formed by an air jet-syringe pump droplet generator. With this apparatus, the cell-sodium-alginate suspension was extruded through a 22-gauge needle located inside a sheathed tube (3 mm I.D.) through which air flowed at a controlled rate (9 L/min). As liquid droplets were forced out of the end of the needle by the syringe pump (at 20 cc/hr), the droplets were pulled off by the shear forces set up by the rapidly flowing air stream. The needle tip was kept 8 cm above the surface of the $CaCl_2$ solution surface to ensure that uniform, spherical gel droplets were formed with a diameter of about 300–1000 microns. A sample of the gelled microbeads was examined for size and shape consistency using a dissecting microscope (Wild Heerbrugg Model M8) fitted with a calibrated eye-piece. After transferring the calcium alginate gel beads, containing the immobilized cells, to a 50 mL plastic centrifuge tube with a conical bottom, the beads were washed with 30 mL each of 0.1% (w/v) CHES and 1.1% (w/v) $CaCl_2$ solutions. The supernatant volume was reduced after each washing using a vacuum aspirator. With the alginate-PLL microcapsule system, a semi-permeable capsule membrane was formed by reacting the gel droplets with an aqueous 0.05% (w/v) PLL solution (Mv of PLL=22,000) for 6 minutes. After the addition of the PLL solution, the centrifuge tube was capped and manually rocked end-to-end for the duration of the reaction to keep the capsules from sticking together. The resultant microcapsules, 300–1000 microns in diameter, were then washed with 30 mL each of 0.1% CHES and 1.1% $CaCl_2$ and with two 30 mL aliquots of isotonic saline. Contact with 30 mL of 0.03% (w/v) sodium alginate solution for 4 minutes formed an outer layer on the capsules. The interior of the microcapsules was liquified with 30 mL of a 0.05 M sodium citrate solution for six minutes. The microcapsules, 400–1400 microns in diameter, were washed several times in saline to remove excess citrate and then divided into five 1 mL aliquots. Each aliquot was incubated in 10 mL DMEM medium in a 25 $cm^3$ culture flask at 37° C. in an Isotemp Series 400 $CO_2$ Incubator (model 413D, Fisher Scientific Co., Nepean, Ontario).

EXAMPLE 2

Microencapsulation of Hybridoma Cells in Multiple Membrane Capsules

A modified microencapsulation technique was employed to reduce the viscosity of the intracapsular alginate solution by removing part of the intracapsular alginate core during the encapsulation procedure and also by allowing the capsules to expand to a greater extent in the citrate step. Initially, the same procedure was followed as with the single membrane capsules, except that a high molecular weight PLL ($\overline{M}=200,000$) was employed in the membrane forming step in order to produce a capsule with a high membrane molecular weight cut-off as a result of a greater degree of capsule swelling. Then, after the citrate step, the microcapsules were incubated in saline for 30 minutes to allow sodium alginate to diffuse out of the capsules and the capsules to swell. The membrane molecular weight cut-off was subsequently reduced by reacting the microcapsules with 30 mL of 0.04% (w/v) PLL of $\overline{M}=22,000$ for 6 minutes. The modified (multiple membrane) microcapsules, containing hybridoma cells, were then rinsed three times with 30 mL aliquots of isotonic saline and reacted with 30 mL of 0.03% sodium alginate solution for 4 minutes. The microcapsules were washed two times with 30 mL portions of saline to remove non-bound alginate, and divided into five 1 mL aliquots. Each microcapsule aliquot was incubated in 10 mL DMEM medium at 37° C. In some experiments the PLL solution was replaced by modified chitosan.

Examination of the microcapsules under a dissecting microscope revealed that the capsules swelled for up to two hours immediately after the interior was liquified. The swelling phenomenon was found to be directly proportional to the PLL molecular weight and inversely proportional to the alginate-PLL reaction time. In the standard encapsulation procedure, a single preparation of calcium alginate beads, diameter 600 microns, for example, produced single membrane capsules with a diameter of 840 microns and double membrane capsules with a diameter of 1020 microns. The latter having 80% greater intracapsular volume.

EXAMPLE 3

Control of Capsule Membrane Molecular Weight Cut-Off

The molecular weight cut-off of the alginate-PLL capsule membrane, was controlled by modulating 1: the alginate-PLL reaction time from 3 minutes to 40 minutes, 2: the $\overline{M}$ of the PLL from 14,000 to 525,000, and 3: the concentration of PLL (used in the encapsulation procedure) from 0.04 to 0.15% (w/v) (i.e. 0.07 to 0.29 mg PLL/cm$^2$ alginate bead surface). The ability of the capsule membrane to exclude proteins of specific molecular weight was then assessed using protein diffusion studies. In these experiments approximately 5 mL of single membrane microcapsules were prepared as previously described with the exception that the hybridoma cells were omitted from the encapsulation procedure. A protein standard (Gel Filtration molecular weight calibration kit) was dissolved in 3-4 mL of saline. Approximately 1 mL of the protein solution was mixed with the supernatant containing the 5 mL of capsules and 5 mL of saline by slowly tilting the centrifuge tube end-to-end several times. At intervals of 0.25 to 1.00 hour, samples of the supernatant were removed and their absorbance measured at 290 nm over a three hour period. The membrane was deemed impermeable to the protein if there was 100% rejection of the diffusing protein over a three hour period. Controls were performed by replacing the 5 mL of capsules with saline, alginate beads or ruptured capsules. To assess the effect of protein adsorption onto the microcapsules or centrifuge tube, some of the diffusion experiments were performed in triplicate, with the same set of capsules.

The alginate-PLL reaction time studies, with bovine albumin (MW=66,000) as the diffusing protein and with PLL of $\overline{M}$=21,000, showed that the membrane molecular weight cut-off decreased as the alginate-PLL reaction time increased, only at an alginate-PLL reaction time of 40 minutes was the albumin completely excluded from the capsules. Control experiments with the capsules being replaced by 5 mL of saline, alginate or ruptured capsules showed that the protein diffusion results were not due to protein adsorption onto the capsule membranes or centrifuge tube.

The results of diffusion studies performed with capsules prepared with PLL of different $\overline{M}$ and at a constant alginate-PLL reaction time of six minutes showed that as the Mv of the PLL decreased, the capsule membrane molecular weight cut-off decreased from about $300 \times 10^3$ (at PLL of Mv=525,000 to about $60 \times 10^3$ (at PLL of Mv=14,000). The membrane was deemed impermeable to the diffusing protein if there was no significant change in the absorbance of the protein solution, compared to the controls, over a three hour period. Each experiment was repeated 3 to 5 times. In some experiments, while one batch of capsules completely excluded the diffusing protein, a different preparation of the same type of capsules allowed some of the protein to diffuse across the membrane. These membranes were classified as borderline in terms of being able to exclude the diffusing protein.

When the PLL concentration was increased while keeping the $\overline{M}$ of the PLL and the alginate-PLL reaction time constant, the molecular weight cut-off of the capsule membrane apparently decreased. Two sets of microcapsules, prepared with PLL of $\overline{M}$=65,000 and PLL concentrations of 0.08 and 0.029 mg of PLL per cm$^2$ of alginate bead surface, were tested. The capsules prepared with the high PLL concentration excluded the protein standard while those capsules made with the lower PLL concentration did not.

The physical strength of the capsules was also found to depend on the $\overline{M}$ of the PLL and the alginate-PLL reaction time. As the $\overline{M}$ of the PLL was increased, the physical durability of the membrane compared by pinching the capsules with fine-tip tweezers, decreased. With the single membrane capsules, with PLL of $\overline{M}$ higher than 120,000, it was common, at the end of the encapsulation process, to find 10-20% of the capsules ruptured. . Below $\overline{M}$=120,000, however, the capsule membranes were strong and flexible. At low $\overline{M}$ of PLL (14,000-25,000), the membranes were thick and leathery in texture and were difficult to rupture. An increase in membrane strength was also observed when the alginate-PLL reaction time was increased. This effect was most prominent with PLL of $\overline{M}$ less than 65,000 but virtually disappeared with microcapsules prepared with PLL of $\overline{M}$ between 200,000 and 525,000

EXAMPLE 4

Cell Culture Studies

Monoclonal antibody-producing hybridoma cells (mouse $AcV_1$-$II_{20}$ were immobilized in single and multiple-membrane alginate-PLL microcapsules, and cultured for 3 weeks in DMEM medium at 37° C. The medium was changed daily. Hybridoma cells in suspension culture were used as controls. Cell density, monitored about every 2 days, was determined by randomly removing ten capsules from the growth medium using a Pasteur pipette. After measuring the average capsule diameter (this was required for the determination of the intracapsular volume) excess liquid surrounding the capsules was wiped away with an absorbant tissue and about 100 mL of isotonic saline was added. The capsules were then ruptured by squeezing them with a pair of fine forceps. A drop of this solution, mixed by drawing into a fine-bore pipette, was then placed on a haemacytometer slide and the number of cells in the 0.1 mm$^3$ well was counted with the aid of a dissecting microscope. This experiment was repeated three times for each cell density determination. Cell viability was assessed by staining the cells for 1 minute in 0.2% Trypan Blue dye. Only the nuclei of dead cells taken up the stain.

At the end of the three week culture period, the microencapsulated hybridoma cells were removed from the medium and washed three times with 30 mL saline. The capsules were ruptured by passing them several times through a narrow (100 μm I.D. pipette. The suspension was the centrifuged at 2000 rpm for 10 minutes to separate the cells and capsule debris from the protein product. The intracapsular solution was stored in an Eppendorf microcentrifuge tube at 4° C. prior to analysis of protein concentration and monoclonal antibody content.

Figure 2:
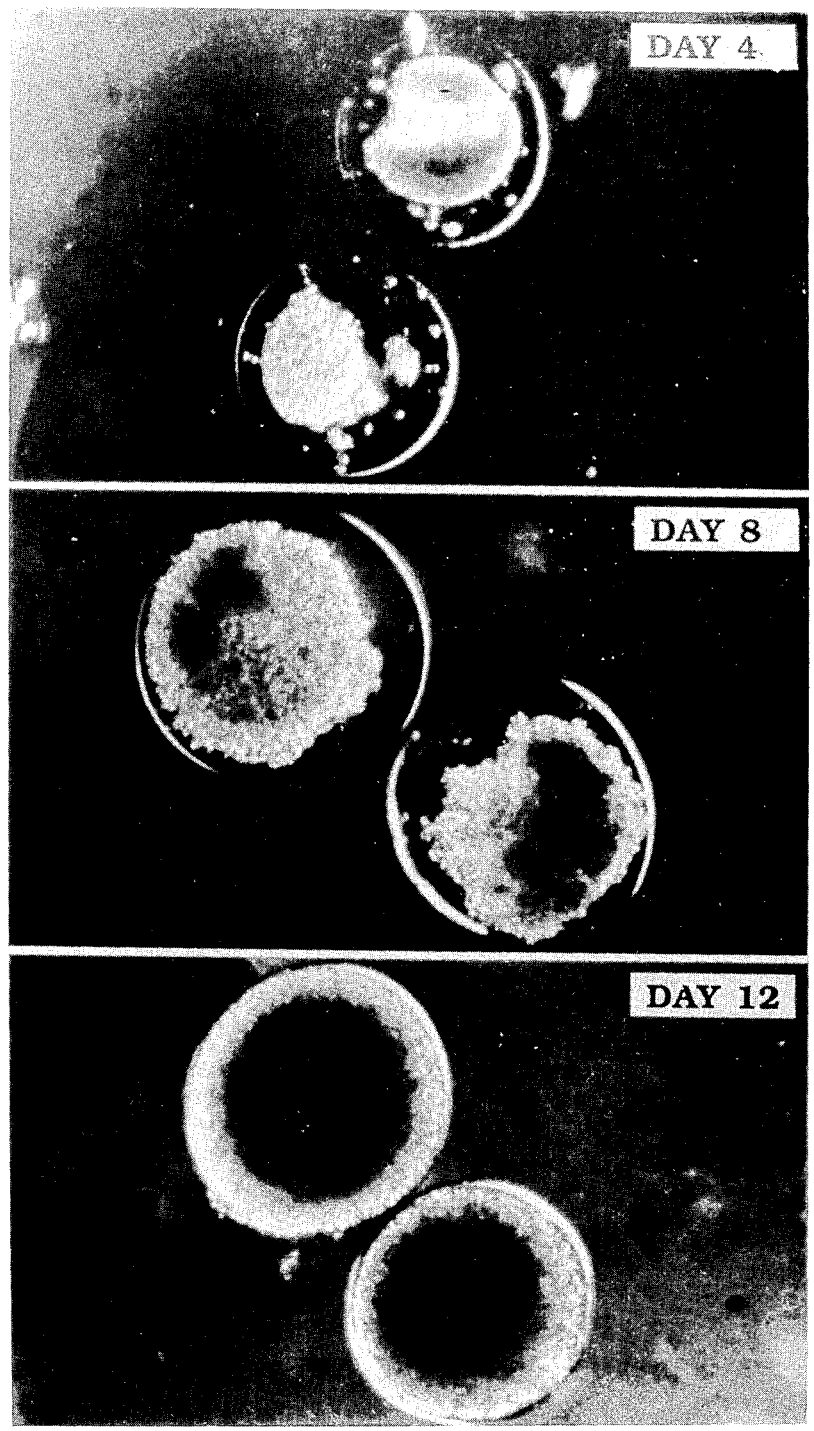
FIG. 2 is a photograph illustrating tissue culture of encapsulated mouse hydridoma cells using multiple membrane alginatePLL microcapsules in DMEM medium at 37° C. over a 12 day period.

Mouse hybridoma cells encapsulated in single alginate-PLL membranes with a molecular weight cut-off of 60,000 were relatively evenly dispersed in the intracapsular alginate matrix at a cell density of about $10^6$ cells/mL. By day 7 of the culture study, the presence of large cell masses was noted inside the capsules. These cell masses appeared to be distributed mainly near the interior surface of the capsules. By day 14 of the intracapsular cell density had stabilized at $2 \times 10^7$ cells/mL. From FIG. 1 it can be seen that the entire capsule volume was not used for cell growth. Multiple membrane capsules' on the other hand, gave final intracapsular cell densities of $6 \times 10^7$ cells/mL (FIG. 2 and Table 1). It can be seen that the entire volume of the capsule was occupied by cells.

TABLE 1

| TYPE OF CAPSULE | CELL DENSITY (CELLS/ML CAPSULE) |
|---|---|
| Suspension (control) | $1 \times 10^6$ |
| Single membrane | $2 \times 10^7$ |
| Multiple membrane | $10 \times 10^7$ |

EXAMPLE 5

Recovery and Analysis of Intracapsular Protein and Monoclonal Antibody

The molecular weight distribution of the recovered protein product was assessed by gel filtration. Samples (0.15 mL) of intracapsular protein were loaded on a Sephadex G-200 column (2 cm diam.×15 cm, and eluted at 13 mL/hr using saline (150 mM NaCl) containing 0.05% (w/v) sodium azide as an antibacterial agent. Samples, 0.5 mL, were collected with the aid of a fraction collector (LKB, Ultrorac 11) and assayed for protein concentration and monoclonal antibody activity. Protein concentration was assessed using the Bio-Rad Protein Assay. Several dilutions of the intracapsular protein solution were prepared. Undiluted samples (0.8 mL and appropriately diluted samples were placed in clean dry test tubes. A sample of buffer (PBS), 0.8 mL, was also placed in a "blank" test tube. After adding a Dye Reagent Concentrate (0.2 mL) to each sample, the solutions were mixed by gentle inversion. After a period of 30 minutes, the optical density was read at 595 nm versus the reagent blank. The unknowns were then read from a standard curve which had been prepared with dilutions of protein (Bovine $\gamma$-Globulin) standard of known concentration.

Sephandex G-200 Gel filtration of the intracapsular solution showed that the multiple membrane capsules produced 300% more protein product per mL of capsules than the single membrane capsule. The total protein recovered was determined from the area under the curve of protein conc. from $V_e/V_o = 1.5$ to $V_e/V_o = 1.8$. An IgG antibody was used as a standard and came out at an elution volume of 1.65 (where $V_{e=elution\ volume}$ & $V_o$ = void volume).

Monoclonal antibody product recovered from multiple membrane capsules was about 500% greater than for the single membrane capsule (Table 2). In addition, there was significantly less loss of antibody (into the supernatant) from the multiple membrane capsule as indicated by the low antibody concentration in the supernatant. These results indicate that in cell culture engineering multiple membrane capsules are significantly better for producing and recovering high value biological products such as monoclonal antibodies.

TABLE 2

| | ANTIBODY CONCENTRATION* ($\mu$g/mL) | ANTIBODY RETENTION BY CAPSULE (% of total)*** | HYBRIDOMA CELL LINE |
|---|---|---|---|
| SUSPENSION (CONTROL) | 10–100 | — | — |
| SINGLE MEMBRANE CAPSULE | | | |
| .Rupp | 1000–4000** | — | 100-83; 102-84 |
| .Goosen | 200–900** | 40–50 | $AcV_1\text{-}II_{20}$ |
| MULTIPLE MEMBRANE CAPSULE | 500–5000** | 70–80 | $AcV_1\text{-}II_{20}$ |

*care must be taken when comparing antibody concentrations since different cell lines have different specific productivities ($\mu$g antibody produced /$10^6$ cells · day)
**intracapsular antibody concentration
***antibody retention by capsule = $\frac{\text{weight of intracapsular antibody}}{\text{weight of intracapsular + extracapsular antibody}} \times 100\%$.

EXAMPLE 6

Assessment of Intracapsular Alginate Content

The apparent residual intracapsular alginate content of the multiple membrane alginate-PLL capsules was determined by preparing 5 mL of capsules without cells, decanting of the extracapsular liquid, weighing the wet capsules, drying the same capsules in air and under vacuum and then weighing the dried capsules. The residual intracapsular alginate concentration was determined by dividing the dry capsule weight by the wet capsule weight. Alginate beads and single membrane capsules were used as a control and reference respectively. As can be seen in Table 3 the multiple membrane microcapsules contained about 23% less alginate than the standard 60,000 molecular weight cut-off microcapsule.

TABLE 3

| | RESIDUAL ALGINATE CONTENT OF CAPSULE | |
|---|---|---|
| | (% w/w)* | %** |
| Alginate Beads (control) | 2.23 | 100 |
| Single Membrane | 1.98 | 89 |
| Multiple Membrane | 1.49 | 67 |

* $\frac{\text{dry wt}}{\text{wet wt}} \times 100\%$

** $\frac{1.98}{2.23} \times 100\% = 89\%$

EXAMPLE 7

Chemically Modified Chitosan as an Alternative Membrane Forming Polymer to PLL

The molecular weight of the chitosan was reduced by a nitrite oxidation reaction. A number of 0.1% chitosan aliquots were reacted overnight with a 0.1 wt % solution of sodium nitrite at room temperature after vigorous shaking, over a molar ratio range of 0.01 to 0.10 moles of nitrite to chitosan. Finally, each digested 10 grams to 0.1 wt % chitosan aliquot was diluted to 100 grams with distilled water, the pH adjusted to 6.5, and applied to encapsulation.

Chitosan derivatives prepared by reaction with 0.03, 0.05, 0.07 moles of sodium nitrite per mole of chitosan were examined to determine their degree of deacetylation, molecular weight, and infrared profile. The technique of Aiba (23) was employed to determine the degree of N-deacetylation, the percentage of polymer units containing the pendant amine group of chitosan and not the acetyl group found in chitin. To calculate the viscosity average molecular weight, samples of concentrations 0.100, 0.050, and 0.010 grams of polymer per decilitre were prepared. A sample of each solution was loaded into a Cannon-Fenske routine viscometer, size no.=50, following the procedure outlined in ASTM Standard D 445 (1973). The viscometer was then suspended in a constant temperature bath at $25\pm0.1°$ C. It was then possible to calculate the viscosity average molecular weight by employing the Mark-Houwink relationship (Table 4).

Chitosan-alginate microcapsules were prepared by replacing the PLL solution with 30 mL of 0.1% (w/v) chitosan derivative ($\overline{M}=2.4\times10^5$, pH 6.5). An alginate-chitosan reaction time of 20 minutes was employed. The microcapsule core was reliquified with 15 mL of 0.05 M Na citrate solution for 3 minutes. The molecular weight of the base chitosan chain was reduced to allow for a more effective penetration of chitosan into the calcium alginate gel matrix and thus presumably increasing capsule membrane thickness and strength. In the case of chitosan of $\overline{M}=6.6\times10^5$, very thin and flexible membranes were formed with little strength increase over unmodified chitosan (Table 4). For the sample reacted with chitosan of $\overline{M}=1.2\times10^5$, the capsules formed were paraboloid in shape, with very thick, inflexible membranes surrounding the collapsed capsules. In contrast, capsules prepared with the intermediate molecular weight derivative $\overline{M}=2.4\times10^5$ were spherical with a reasonably thick and durable membrane. Capsules were also prepared with chitosan of $\overline{M}=1.6\times10^5$ and $3.3\times10^5$. In both cases, excellent capsules were prepared with strong flexible membranes.

For chitosan-PLL-alginate microcapsules, the first PLL solution in the encapsulation procedure was replaced with 0.1 wt % of reduced MW chitosan and reacted for 20 minutes: then washed with saline and reacted with 0.03 wt % Na alginate for 4 minutes. After being washed with saline, the capsules were reacted with PLL (0.05 wt %, $\overline{M}=22{,}000$) for 6 minutes to stabilize the membrane. An alternate batch of chitosan-/alginate/PLL capsules was prepared, as above, except that the order of polymer application was reversed. All three types of capsules were stable in saline.

Microcapsules were also prepared by mixing the cells with sodium alginate and then extruding the suspension directly into a chitosan solution. The intermediate, calcium alginate gel forming step was omitted. The encapsulated cells retained viability.

TABLE 4

| FORMATION OF CHITOSAN MICROCAPSULES | | | |
|---|---|---|---|
| CHITOSAN DERIVATIVE APPLIED IN ENCAPSULATION (Molar Ratio of Nitrite to Chitosan) | CHITOSAN MOLECULAR WEIGHT $\overline{M}v \times 10^5$ | MODIFIED CHITOSAN/ ALGINATE MEMBRANE DURABILITY | |
| | | Strength | Flexibility |
| 0.10 | 1.2 | ++++ | + |
| 0.07 | 1.6 | +++ | +++ |
| 0.05 | 2.4 | ++ | ++++ |
| 0.03 | 3.3 | + | ++ |
| 0.01 | 6.6 | − | − |

Scale:
Strength + = Weak ++++ = Strong
Flexibility + = Fragile ++++ = Very Flexible

EXAMPLE 8

Encapsulation of Virally Infected Insect Cells

A sample of AcNPV ts-10, the mutant showing the lowest "leakiness" (i.e. the lowest tendency to express the wild-type phenotype under non-permissive temperatures) was produced by growing wild-type (HR3) AcNPV in the presence of 1-methyl-3- nitro-1-nitrosoguanidine (3 pg/ml) and stored at 4° C. until used. The virus replicated at 27° C. but not at 33° C.

A 1.4% sodium alginate solution was prepared by dissolving 1.4 g of sodium alginate powder (Keltone LV, Kelco, Chicago, IL) in 100 mL of KCl solution (a solution containing 0.85 g of KCl in 100 mL of distilled water will be referred to as KCl solution). The alginate solution was sterilized by heating in a boiling water bath at 100° C. for 15 minutes. A 0.03% sodium alginate solution was prepared by adding 2.1 mL of a 1.4% sodium alginate solution of 97.9 mL of KCl solution. 1.1% and 1.5% $CaCl_2$ solutions were prepared by adding 14.57 g or 19.86 g of $CaCl_2 \cdot 2H_2O$, respectively, to 1000 mL of distilled water. 0.1% CHES (2-(n-Cyclohexylamino) ethane sulfonic acid) (Sigma Chemical Company) was made by dissolving 2.0 g of CHES and 0.51 g of KCl in 100 mL of distilled water. A 0.05 M sodium citrate solution was prepared by dissolving 2.58 g of sodium citrate and 0.85 g of KCl in 200 mL of distilled water.

The pH of the encapsulation solutions was adjusted to 6.2 using NaOH or HCl. All solutions were then sterilized by passing through a 0.22 m filter apparatus under positive pressure (Nalgene Sterilization Filter Unit, Type 2, Nalgene Company Rochester, N.Y.).

Polylysine solutions were prepared by dissolving the appropriate amount of poly(l-lysine) hydrobromide (PLL) (Sigma Chemical Company) in sterile KCl solution.

Single Membrane Microcapsules

Medium from a 75 $cm^2$ sub-confluent flask of cells was carefully removed and about 10 mL of fresh medium was added. The flask was then gently shaken to dislodge the cells from the side. Cells were pelleted by centrifuging at 1000 rpm for 10 minutes and the medium was removed by vacuum aspiration. The pellet was resuspended in three mL of a 1.4% sodium alginate solution. Two millilitres of the alginate/cell suspension was extruded into 30 mL of a 1.5% (w/v) $CaCl_2$. Droplets of this solution were made by an air-jet/syringe-pump droplet generator. The remaining one mL of alginate was used to determine the initial cell density and viability.

Following rinses in 30 mL aliquots each of 0.1% CHES and 1.1% (w/v) $CaCl_2$ and two 30 mL aliquots of KCl solution, the cell-containing beads were reacted with 30 mL of a 0.05% (w/v) PLL solution ($\overline{M}$ of PLL=22000) for 6 minutes. After this, the beads were rinsed with 30 mL portions of 0.1% CHES, 1.1% (w/v) $CaCl_2$ and KCl solution. Reaction with 30 mL of 0.03% (w/v) sodium alginate for 4 minutes formed an outer layer on the membrane. The beads were then washed twice with 30 mL of a KCl solution followed by incubation in 0.05 M sodium citrate for 6 minutes to re-liquify the interior of the capsules. The capsules were washed three times in a KCl solution to remove excess citrate and then incubated (with gentle agitation) in equal volumes of KCl solution and 2x TC100 for 20 to 30 minutes to allow some of the intracapsular alginate to diffuse out of the capsules and to allow the capsules to expand toward their equilibrium state. The capsules were then added to 30 mL of complete TC100 medium and divided into two equal aliquots and incubated at 33° C.

A second type of single membrane microcapsule was made, as before, except that a high molecular weight PLL ($\overline{M}$=270000) was used in the membrane-forming step.

A third type of capsule was also made with a high molecular weight PLL membrane. In this case, however, the cells were resuspended in equal volumes of 1.4% alginate and 2x TC100 growth medium having the composition shown in Table 5 to give a final alginate concentration of 0.7% (w/v).

TABLE 5

COMPOSITION OF INSECT MEDIUM (2X TC100) USED IN ENCAPSULATION PROCEDURE

| COMPONENT | CONCENTRATION (mg/L) |
| --- | --- |
| Inorganic Salts | |
| $CaCl_2.2H_2O$ | — |
| KCl | 5740.0 |
| $MgSO_4.7H_2O$ | — |
| $NaH_2PO_4.H_2O$ | 2014.0 |
| $NaHCO_3$ | 700.0 |
| $MgCl_2.6H_2O$ | — |
| Other Components | |
| Glucose | 2000.0 |
| Bacto Tryptose Broth | 5200.0 |
| Amino Acids | |
| l - Alanine | 450.0 |
| l - Arginine.HCl | 1100.0 |
| l - Asparagine | 700.0 |
| l - Aspartic Acid | 700.0 |
| l - Cystine | 44.0 |
| l - Glutamic Acid | 1200.0 |
| l - Glutamine | 1200.0 |
| l - Glycine | 1300.0 |
| l - Hystidine.HCl.$H_2O$ | 6760.0 |
| l - Isoleucine | 100.0 |
| l - Leucine | 150.0 |
| l - Lysine | 1250.0 |
| l - Methionine | 100.0 |
| l - Phenylalanine | 300.0 |
| l - Proline | 700.0 |
| l - Serine | 1100.0 |
| l - Threonine | 350.0 |
| l - Tryptophan | 200.0 |
| l - Tyrosine | 100.0 |
| l - Valine | 200.0 |
| Vitamins | |
| Biotin | 20.0 |
| Cyanocobalamin | 20.0 |
| Calcium - Pantothenate | 40.0 |
| Folic Acid | 40.0 |
| i - Inositol | 40.0 |
| Niacin | 40.0 |
| p - Aminobenzoic Acid | 40.0 |
| Pyridoxine.HCl | 40.0 |
| Riboflavin | 40.0 |
| Thiamin.HCl | 40.0 |

Multiple Membrane Microcapsules

Initially, the same procedure was followed as with the procedure for encapsulating insect cells in single membrane capsules except that PLL of $\overline{M}$=270000 was used in the initial membrane-forming step. After the citrate step, however, the capsules were incubated in equal volumes of KCl solution and 2x TC100 medium and rocked end-to-end for 20 to 30 minutes to allow the lower molecular weight sodium alginate to diffuse out of the capsules and to allow the capsules to swell. Following three rinses with with KCl solution, the membrane molecular weight cut-off was reduced by reacting the microcapsules with 30 mL of 0.02 to 0.15% (w/v) PLL of Mv =22000. The microcapsules were finally rinsed three times with 30 mL aliquots of KCl solution and then reacted with 30 mL of 0.03% sodium alginate solution for 4 minutes. The microcapsules were washed two times with 30 mL portions of KCl solution to remove un-bound alginate, added to complete TC 100 medium, divided into two equal aliquots and incubated at 33° C.

A second type of multiple membrane microcapsule was made using the procedure just described except that the concentration of the original alginate solution used in the encapsulation procedure was reduced from 1.4% to 0.7% by the addition of 2x TC100 medium.

Insect Cell Culture

Insect cells which had been exposed to the temperature-sensitive virus mutant (ts10) were encapsulated in single and multiple membrane microcapsules to determine if the cells could grow inside the capsules and to assess the ability of the virus to grow and to be retained within the capsules. In these experiments, the medium was first carefully removed from a subconfluent 75 $cm^2$ flask of cells and 3 mL of fresh medium was added. The approximate cell density was then estimated by counting the number of cells in several small areas of the flask using a dissecting microscope with a graticulated eyepiece. The cells were incubated with virus (Multiplicity of Infection (MOI) of 0.05 to 0.10) for about 3 hours, at 33° C., to allow for adsorption (infection of the cells). The MOI refers to the number of infectious units of virus added per cell. This infected cell suspension was then encapsulated as previously described and cultured at 33° C., a non-permissive temperature for ts10 virus replication (viral growth). After 4 days, the encapsulated cells were transferred to a 27° C. incubator to initiate ts10 viral replication. Insect cell density was determined daily by first removing about 50 capsules from the growth medium using a pasteur pipette. After measuring the average capsule diameter (in order to determine the intracapsular volume) excess liquid surrounding the capsules was removed with a hypodermic needle and 300 pL of 0.2% trypan blue dye (in KCl solution) was added and the capsules were ruptured. The cell density in this solution was then determined using a haemocytometer. The actual cell density was calculated by multiplying the above number by the dilution factor ((volume capsules+volume of trypan blue)/(volume of capsules)) and by $10^4$. Determination of cell deinsity was done in triplicate. Samples of the capsules were stored in sterile microcentrifuge tubes in a refrigerator at 4° C. until assayed for virus content.

Toxicity Studies

The membrane-forming polymers (alignate and PLL) and the solutions used in the encapsulation procedure (i.e. KCl solution, 0.1% CHES, 1.5% and 1.1% CaCl$_2$ and 0.05 M sodium citrate) were tested for their biocompatibility (adverse effect on cell viability). In each toxicity study, insect cells were cultured to sub-confluency in 6 cm tissue culture dishes. The medium was then carefully poured off and the cells were then exposed for 1 minute to 4 mL of the encapsulation solutions. Two PLL solutions (PLL of $\overline{M}=22000$ and 270000) were tested at a concentration of 0.05% (w/v). The cells were then washed twice with 5 mL aliquots of KCl solution prior to being incubated for 2 hours in growth medium (TC100) at 27° C. in a humid environment. The medium was poured off and the cells were exposed to 2 mL of 0.2% trypan blue stain in KCl solution. The number of viable (unstained) and nonviable (stained) cells in each of 5 random fields was counted and the percentage of viable cells calculated.

Alginate solutions were tested at various concentrations. The cells were first pelleted and then mixed with different ratios (Table 6) of a 2.0% sodium alginate solution (prepared by dissolving 3 g of alginate powder in 100 mL of KCl solution), KCl solution and 2x TC100 medium (which contained divalent metal ions and 20% (v/v) fetal calf serum) to give final alginate concentrations of 1.5, 1.3, 1.0, 0.75 and 0.50% (w/v). The volume of 2x TC100 was always one-half of the total volume. These solutions were added to a 6-well culture plate and incubated at 27° C. The sixth well contained cells which had been centrifuged and resuspended in TC100. Effects of the alginate were assessed by observing the cells' growth for several days.

TABLE 6
FORMULATION OF ALGINATE SOLUTIONS USED IN TOXICITY TESTS

| PERCENT ALGINATE | VOLUME OF 3% ALGINATE (mL) | VOLUME OF KCl SOLUTION (mL) | VOLUME 2x TC100 (mL) |
|---|---|---|---|
| 1.5 | 5 | 0 | 5 |
| 1.3 | 4.3 | 0.7 | 5 |
| 1.0 | 3.3 | 1.7 | 5 |
| 0.75 | 2.5 | 2.5 | 5 |
| 0.50 | 1.7 | 3.3 | 5 |

Cell pellets were mixed with complete 2x TC100, 3% alginate and KCl solution in the above amounts. The alginate/cell mixtures were then added to a 6-well culture plate and incubated at 28° C. The 6th well contained cells which had been centrifuged and resuspended in complete TC100 and was used as a control.

Results

The capsules produced by the standard single membrane and multiple membrane procedures were spherical in shape and showed no surface irregularities. The cells in the single membrane capsules remained dispersed throughout the volume of the capsule and, after 2 days in culture, became enlarged and dark in colour. Recovery of some of the cells from these capsules and subsequent staining with trypan blue indicated that few cells were living. In contrast, the cells in the multiple membrane capsules tended to settle to the bottom of the capsule, indicating the viscosity of the intracapsular solution was lower. After 2 days in culture, these cells appeared to be healthy (supported by trypan staining) although little sign of growth could be seen. The doubling time of insect cells is between 17 and 24 hours.

The capsules which were produced using a 0.7% alginate/ TC100/cell mixture were non-spherical in shape and tended to have pointed ends, tails and creased sides. This non-sphericity, due to the low concentrations and hence low viscosities of the alginate/cell suspensions, was most prevalent when the concentration was 0.5% and was significantly reduced when increased to 0.6% or 0.7%. The capsules produced with a single, high molecular weight cut-off membrane (and either 0.7% or 1.4% alginate) tended to have weak membranes which broke easily and, consequently, allowed the cells within to escape and proliferate in the growth medium. In those few capsules which did not rupture, the infected cells grew in isolated clumps on the inside surface of the membrane.

Figure 3:
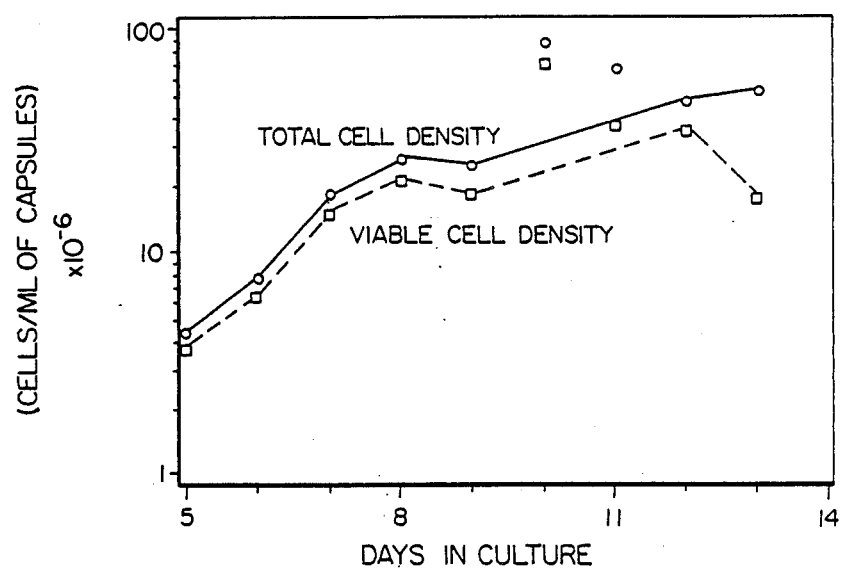
FIG. 3 is a graph illustrating insect cell density against days in culture.

The capsules which possessed a multiple membrane were much stronger and more flexible than their single membrane counterparts as judged by pinching the capsules with fine tipped forceps. Consequently, there were fewer ruptured or broken capsules and significantly reduced number of cells were found in the supernatant. Cells grew and virtually filled the microcapsules reaching final densities of 4 to $5 \times 10^7$ cells/mL (FIG. 3). In comparison, maximum suspension culture densities are at least 10 times lower.

Figure 4:
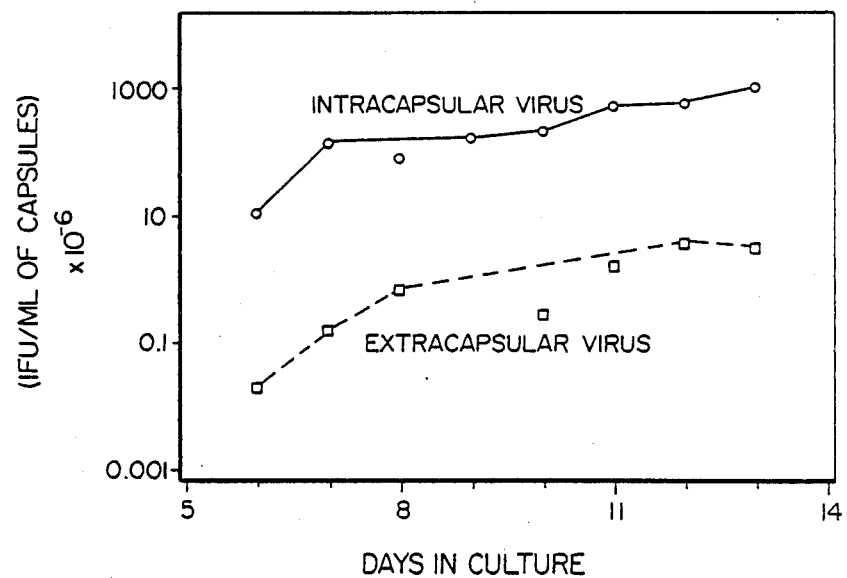
FIG. 4 is a graph illustrating virus concentration against days in culture.

The TCID$_{50}$ assay revealed that the titre of virus in the capsules was about $1 \times 10^9$ infectious units (IFU) per mL and that of the supernatant was about 300 times lower (FIG. 4). This indicates that virtually all of the virus (>99%) was retained within the capsules.

Toxicity Tests

The results of the toxicity tests are summarized in Table 7 and Table 8. None of the solutions (KCl, CHES, CaCl$_2$ and citrate) caused any apparent effect on the growth of the cells. Cells exposed to 1.4% and 0.7% alginate solutions showed some decrease in viability. Cells immobilized in mixtures of sodium alginate and TC100 (final concentrations of 1.5, 1.3 and 1.0% (w/v)) showed little or no growth and usually appeared dark and granular after 2 to 3 days. Trypan blue staining indicated that few, if any cells were viable. Cell growth, however, was observed in the lower alginate/TC100 mixtures (concentrations 0.75 and 0.5% (w/v)). Exposure of the cells to PLL ($\overline{M}=22000$) resulted in virtually no loss of cell viability while 75% of the cells exposed to PLL ($\overline{M}=270000$) showed a loss of viability.

TABLE 7
TOXICITY TESTS: PLL AND ENCAPSULATION SOLUTIONS

| SOLUTION | PERCENTAGE OF CELLS LIVING |
|---|---|
| PLL Solution (0.05% (w/v)) | |
| $\overline{M}v - 22000$ | 100 |
| $\overline{M}v = 270000$ | 24 + 1 |
| Citrate | 100 |
| CHES | 100 |
| KCl | 100 |

TABLE 8
TOXICITY TESTS: CELLS IMMOBILIZED IN ALGINATE

| ALGINATE CONCEN-TRATION | ALGINATE VISCOSITY | OBSERVATIONS |
|---|---|---|
| 1.5% (w/v) | 55 cps | All cells enlarged, and dark most dead |
| 1.3% (w/v) | 40 cps | All cells enlarged, and dark most dead |
| 1.0%% (w/v) | 20 cps | Some cells dark and granular |

TABLE 8-continued

TOXICITY TESTS: CELLS IMMOBILIZED IN ALGINATE

| ALGINATE CONCENTRATION | ALGINATE VISCOSITY | OBSERVATIONS |
| --- | --- | --- |
| | | while some are round and healthy some cells have multiplied to form small masses |
| 0.75% (w/v) | 15 cps | Good cell growth many cell masses |
| 0.50% (w/v) | 8 cps | Good cell growth many cell masses |

Figure 5:
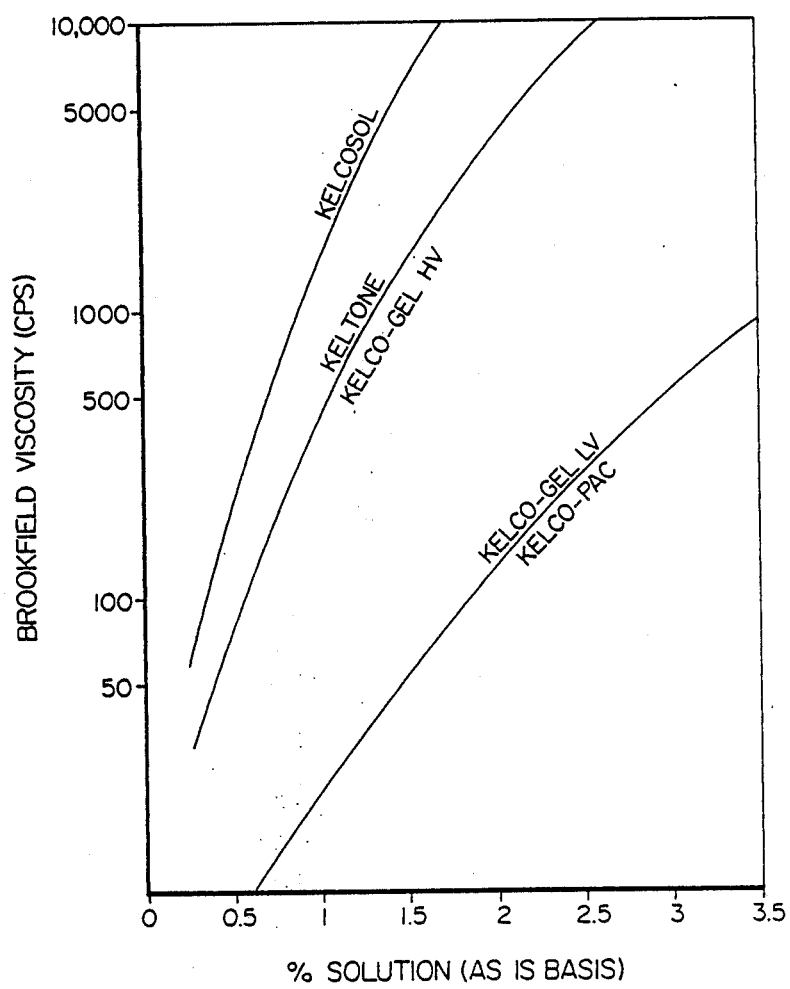
FIG. 5 is a graph illustrating the relationship between alginate concentration and viscosity (Kelco Handbook 2nd ed.).

From the above it is clear that insect cells may not be cultured in either single or multiple membrane capsules when the initial intracapsular alginate concentration is as high as 1.4%, indeed it appears from Table 8 that only at alginate concentrations of 0.75% or less that cell growth occurs. 0.75% alginate corresponds as seen from FIG. 5 to a viscosity of about 15 cps. At this viscosity perfectly spherical droplets are not possible but rather tear-drop shaped droplets are formed. Viscosities in the range from 10-20 cps are, therefore contemplated for insect cell growth. Single membrane capsules (cut-off about 60000) provide a poor cell growth environment. Cell growth is improved in single cell capsules (cut-off about 300000) as it appears that more of the intracapsular alginate (MW=350000) obtained with multiple membrane capsules due to lower intracapsular alginate content. Replication of a temperature-sensitive baculovirus in microcapsules can be controlled by lowering the culture temperature by a few degrees. Thus the insect cells can be cultured to high density at a non-permissive temperature which can then be dropped to initiate virus replication and possibly even recombinant protein production.

We claim:

1. A biocompatible microcapsule, having a diameter of about 400–500 m, comprising:

a macromolecular core material comprising living tissue surrounded by a first biocompatible highly permeable hydrogel membrane consisting of ionically interacted biocompatible materials, having a molecular weight cut-off of about 200–400× $10^3$; and said first membrane being interacted with ionically interacted biocompatible materials to form a second relatively less permeable hydrogel membrane having a molecular cut-off of about 40–80×$10^3$; said first membrane being sufficiently permeable to permit diffusion therethrough of that portion of a water soluble cross-linkable gelling agent used to suspend said living tissue and having a molecular weight of less than 200–400 ×$10^3$, and permitting expansion of said microcapsule towards an equilibrium state; and said second membrane being sufficiently permeable to permit nutrients to flow from a medium in which said microcapsule is placed into said microcapsule to sustain said living tissue, and sufficiently impermeable to retain said living tissue and any high molecular weight product thereof within the microcapsule.

2. A microcapsule as claimed in claim 1 wherein said living tissue is selected from islets of langerhans, liver cells, blood cells, plant cells and hydridoma cells.

3. A microcapsule as claimed in claim 1 wherein said first and second membranes are formed by reaction between a polymeric material having positively charged groups and a polymeric material having negatively charged groups.

4. A microcapsule as claimed in claim 3 wherein said positively charged polymeric material contains amino groups and the negatively charged polymeric material contains carboxyl or hydroxyl group.

5. A microcapsule as claimed in claim 4 wherein said first and second membranes are formed from an alkali metal alginate and a polyamino acid.

6. A microcapsule as claimed in claim 5 wherein said alkali metal alginate is sodium alginate and said polyamino acid is poly-l-lysine.

7. A method of encapsulating living tissue within two semi permeable hydrogel membranes which comprises:

(a) mixing said living tissue with an aqueous solution of water soluble polymeric material which can be reversibly gelled and which has free acid groups.

(b) forming said mixture into droplets and gelling said droplets in a hardening agent;

(c) forming a first biocompatible highly permeable hydrogel membrane about said first gelled droplets to produce a first microcapsule by reaction with a polymer containing free amino groups; said first membrane having a molecular weight cut-off of 200–400×$10^3$;

(d) suspending said first microcapsule in a medium which reliquifies said water soluble polymeric material;

(e) incubating said first microcapsule in an aqueous medium for sufficient time to allow at least one third of that portion of said water soluble polymeric material having a molecular weight of less than 200–400×$10^3$ to diffuse out of said microcapsule, and to allow said microcapsule to expand towards an equilibrium state;

(f) reacting said incubated first microcapsule with a polymer containing positively charged groups to thereby form an interacted relatively less permeable hydrogel membrane having a molecular weight cut-off of 40–80×$10^3$; and (g) incubating said living tissue within said interacted microcapsule in a nutrient medium; said interacted membrane being sufficiently permeable to permit passage of nutrients and sufficiently impermeable to retain said tissue and any high molecular weight products thereof within said second microcapsule.

8. The method of claim 7 wherein said living tissue is selected from islets of Langenhans, liver cells, blood cells and hybridoma cells, insect cells and plant cells.

9. The method of claim 7 wherein said water soluble polymeric material is a polysaccharide gum.

10. The method of claim 9 wherein said polysaccharide gum is an alkali metal alginate.

11. The method of claim 10 wherein said alginate is sodium alginate.

12. The method of claim 7 wherein said polymer containing amino groups is a polyamino acid.

13. The method of claim 12 wherein said polyamino acid is poly-l-lysine.

14. A microcapsule as claimed in claim 2 wherein said second membrane is a separate membrane over said first membrane.

15. A microcapsule as claimed in claim 1 wherein said second membrane is integral with said first membrane.

16. A microcapsule as claimed in claim 2 wherein said insect cell is a temperature sensitive baculovirus infected insect cell.

17. A microcapsule as claimed in claim 16 wherein said insect cell is *spodoptera frugipada.*

18. A microcapsule as claimed in claim 17 wherein said baculovirus is ts-10 *Autographa californica* Nuclear polyhedrosis Virus.

19. The method of claim 8 wherein said insect cell is a temperature sensitive baculovirus infected insect cell.

20. The method as claimed in claim 19 wherein said insect cell is *spodoptera frugipada.*

21. The method of claim 20 wherein said baculovirus is ts-10 *Autographa californica* Nuclear polyhedrosis virus.

22. The method of claim 21 wherein said water soluble polymeric material is sodium alginate, having an intracapsular concentration of less than 0.75% (w/v).

23. The method of claim 21 wherein said watersoluble polymeric material is sodium alginate having a viscosity in the range 10–20 cps.

24. The method of claim 23 wherein said sodium alginate has a viscosity of about 15 cps.

* * * * *